(12) United States Patent
Takahashi et al.

(10) Patent No.: US 8,942,458 B2
(45) Date of Patent: Jan. 27, 2015

(54) METHOD FOR DISTINGUISHING AND SORTING OF CELLS AND DEVICE THEREFOR

(75) Inventors: Toru Takahashi, Tokyo (JP); Ken Tsukii, Tokyo (JP); Jie Xu, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 667 days.

(21) Appl. No.: 13/001,128

(22) PCT Filed: Jun. 19, 2009

(86) PCT No.: PCT/JP2009/061219
§ 371 (c)(1),
(2), (4) Date: Apr. 6, 2011

(87) PCT Pub. No.: WO2009/157385
PCT Pub. Date: Dec. 30, 2009

(65) Prior Publication Data
US 2011/0177544 A1 Jul. 21, 2011

(30) Foreign Application Priority Data
Jun. 27, 2008 (JP) ................ 2008-168817

(51) Int. Cl.
*G06K 9/00* (2006.01)
*G01N 15/14* (2006.01)

(52) U.S. Cl.
CPC ...... *G01N 15/147* (2013.01); *G01N 2015/1438* (2013.01); *G01N 2015/1493* (2013.01); *G01N 2015/1497* (2013.01)
USPC .......... 382/133; 435/173.9; 435/325; 356/39; 356/335; 356/336; 356/432; 356/441; 356/442; 356/625; 382/134

(58) Field of Classification Search
None
See application file for complete search history.

(56) References Cited

U.S. PATENT DOCUMENTS

| | | | | |
|---|---|---|---|---|
| 5,047,963 | A * | 9/1991 | Kosaka .................. | 702/128 |
| 5,312,535 | A | 5/1994 | Waska et al. | |
| 8,211,708 | B2 * | 7/2012 | Tsukii et al. ............ | 436/171 |
| 2005/0207940 | A1 | 9/2005 | Butler et al. | |
| 2006/0004541 | A1 | 1/2006 | Miyamoto | |
| 2006/0139638 | A1 | 6/2006 | Muller et al. | |
| 2009/0198168 | A1 * | 8/2009 | Hiruma et al. .......... | 604/6.08 |

FOREIGN PATENT DOCUMENTS

| | | | |
|---|---|---|---|
| JP | 63-126480 | | 5/1988 |
| JP | 7-270302 | | 10/1995 |
| JP | 2973387 | | 9/1999 |
| JP | 2003304867 | A * | 10/2003 |
| JP | 2006-17497 | | 1/2006 |
| JP | 2006-517292 | | 7/2006 |
| JP | 2007-504446 | | 3/2007 |
| JP | 2008-292448 | | 12/2008 |
| WO | WO 2007135896 | A1 * | 11/2007 |

OTHER PUBLICATIONS

JP 2003304867 (Oct. 2003) Derwent English Abstract. 3 pages.*
JP 2003304867 (Oct. 2003) Raw Machine Translation. 20 pages.*
English Translation of JP 2003304867A. Oct. 2003. 51 pages.*
Combined Chinese Office Action and Search Report issued Nov. 29, 2012, in Patent Application No. 200980124706.6 (with English-language translation), 21 pages.
S. Navarro, et al., "The cytotoxicity of eosinophil cationic protein/ribonuclease 3 on eukaryotic cell lines takes place through its aggregation on the cell membrane", Cellular and Molecular Life Sciences, vol. 65, 2008, pp. 324-337.
Andre C. Romano, et al., "Different Cell Sizes in Human Limbal and Central Corneal Basal Epithelia Measured by Confocal Microscopy and Flow Cytometry", Investigative Ophthalmology & Visual Science, vol. 44, No. 12, Dec. 2003, pp. 5125-5129.
Walter Giaretti, et al., "A New Method to Discriminate G1, S, G2, M, and G1 Postmitotic Cells", Experimental Cell Research, vol. 182, 1989, pp. 290-295.
Atsunori Oga, "Analysis for Cell Cloning Generation", Cell Technology Additional Volume, Experimental Protocol Series, New Edition Flow Cytometry Free-From a Multi-Color Analysis to a Clone Sorting-, pp. 113-115.
Notice for a Reason of Rejection issued Mar. 29, 2013 in Japanese Patent Application No. 2010-517977 (with English translation), 8 pages.
Office Action mailed Oct. 22, 2013, in Chinese Patent Application No. 200980124706.6 (with English-language translation).
Office Action issued Jul. 8, 2014, in Chinese Patent Application No. 200980124706.6 (with English-language Translation).

* cited by examiner

*Primary Examiner* — Allison Fox
*Assistant Examiner* — Susan E Fernandez
(74) *Attorney, Agent, or Firm* — Oblon, Spivak, McClelland, Maier & Neustadt, L.L.P.

(57) ABSTRACT

A method for distinguishing and sorting cells characterized by comprising distinguishing and sorting a specific cell mass or a part of the cells in the cell mass with the use of transmitted light data reflecting the morphological characteristics of the cells such as size and shape optionally together with side-scattering light data reflecting the characteristics of the internal structure of the cells. The part of the cells in the specific cell mass as described above are at the G1 stage or at a part of the M stage in the cell cycle. A part of the cells at the G1 stage are referred to as the left bottom line in an analytical dispersion diagram of the cells wherein the abscissa indicates the transmitted light data, while a part of the cells at the M stage are referred to as the right bottom line in the analytical dispersion diagram of the cells wherein the abscissa indicates the transmitted light data.

5 Claims, 14 Drawing Sheets

FORWARD SCATTERING LIGHT

PARAMETERS OF TRANSMITTED LIGHT INFORMATION

PEAK OF TRANSMITTED LIGHT

METHOD FOR DISTINGUISHING AND SORTING OF CELLS AND DEVICE THEREFOR

TECHNICAL FIELD

The present invention relates to a method and device for distinguishing and sorting cells, and in particular, to a method and device for distinguishing and sorting cells with the use of only transmitted light information reflecting either or both of the morphological characteristics of cells such as size and shape and the characteristics of the internal structure of cells such as nucleus and cytoplasm, or with the use of both such transmitted light information and side-scattering light information reflecting the characteristics of the internal structure of cells.

BACKGROUND ART

A technique of flow cytometry has been used to analyze individual cells in which a cell suspension liquid is allowed to flow fast and irradiated with laser light and measurement is performed. A flow cytometer is known to be able to measure the relative size, the shape, and a difference in the internal structure of individual cells, and the fluorescent intensity and the type of fluorescence by performing fluorescent labeling, and thereby to be able to analyze the existence of cells and/or a cell cluster ratio of various cells in a cell cluster in a short time.

It is set in a manner such that a cell suspension liquid is made to flow fast along the center of a sheath liquid (sheath flow) and the flow is narrowed so that the cell suspension liquid passes through a conical flow passage, which results in that individual cells flow in line. If the cells that are flowing in line are irradiated with laser light, scattering light or fluorescence are emitted from the cells that are passing. An exposure time during which the cell is irradiated with laser light is merely several microseconds. Accordingly, damage to the cell is not problematic at all. The scattering light from the cell is detected as a forward scatter (FSC) in the same direction as a laser beam and a side-scattering light (SSC) at an angle of 90° to the laser beam. The FSC and SSC vary in light intensity, reflecting the size of a cell and the complexity of the internal structure of a cell, respectively. Fluorescence is the light radiating in a direction of an angle of 90° like the side-scattering light (SSC) and is extracted after splitting with the use of an optical filter. So, respective wavelength components thereof are detected.

For example, laser light is used as excitation light and irradiated onto a cell to detect a fluorescent pigment. A fluorescent pigment absorbs a certain wavelength and converts high energy light (short wavelength) to lower energy light (long wavelength). Each fluorescent pigment has the unique excitation wavelength distribution and the emission wavelength distribution. That is, it absorbs wavelengths of light in a certain range but emits radiating light (fluorescent light) with wavelengths in a certain range. The intensity of the obtained fluorescent light (fluorescent intensity) is measured using a detector, and the obtained value is converted into a digitized form and represented in a site gram or a histogram, together with the fluorescent intensities of other cells. For example, SITEGRAM shows information of scattering light and fluorescence that can be obtained from a cell, on the two-dimensional coordinate. In the histogram, for example, the abscissa axis indicates the intensity of light and the vertical axis indicates the number of cells.

As described above, as illustrated in FIG. 8, the conventional Flow Cytometer (FCM) acquires and analyzes measurement values of scattering light to recognize the size of cells and the difference in the internal structure of cells. As the scattering light, both forward scatter and side-scattering light are respectively acquired.

A cell cycle is the course that a daughter cell which has been produced by cell division becomes a mother cell and produces new daughter cells by its own cell division. The cell cycle can be divided into G1 phase, S phase, G2 phase, and M phase. Chromosome increases in number during the G2 and M phases in particular, so that the G2 and M phases are featured in that a cell nucleus or a cell grows bigger. Some specific cells such as stem cells are known that the size ratio of a cell nucleus to a cell is higher than those of general cells.

Patent Document 1: Japanese Patent No. 2973387 (Japanese Patent Application Laid-Open No. 6-323987)

Non-patent Literature 1: Cell Technology additional volume, Experimental Protocol Series, "New Edition Flow cytometry Free—from a multi-color analysis to a clone sorting—," p. 113, (published by Shujunsha Co., Ltd, supervised by Hiromitsu Nakauchi).

DISCLOSURE OF THE INVENTION

Problems to be Solved by the Invention

A conventional cell analyzer, for example, a flow cytometer analyzes the size of a cell by forward scattering light information. However, it is problematic in that analysis accuracy is low and the size of a cell cannot be distinguished clearly. For such a reason, it was necessary to stain DNAs of a cell nucleus for an analysis of the cell cycle. However, it has a problem in that cells perish due to staining if DNAs of the cell nucleus are stained. That is, there are problems in that cells cannot be sorted accurately for each phase of a cell cycle without staining and living cells at a specific phase of a cell cycle cannot be sorted.

On the other hand, in sorting of stem cells or cancer stem cells that is required for development of medicines and regenerative medicines, cells are sorted utilizing the feature that stem cells or cancer stem cells discharge fluorescent chemicals outside themselves. However, the fluorescent chemicals cause damages to the stem cells•cancer stem cells. This has a bad influence on inducing differentiation of stem cells•cancer stem cells.

Moreover, conventional cell recognition and analysis has been performed by an antibody•antigen reaction on the cell surface. However, even in the case of using the antibody•antigen reaction on the cell surface, cells are also damaged by the antibody•antigen reaction. Moreover, there is a problem in that, if no antibodies are present, cells cannot be recognized.

Therefore an object of the invention is to provide a method and device for distinguishing and sorting cells that can recognize a cell cycle of a living cell and a specific cell such as a stem cell, without staining nuclei of cells, giving damages to cells, and causing cells to perish.

Means for Solving the Problems

The inventors made eagerly a series of research to solve the above-mentioned conventional problems. As a result, it has been found that a cell cycle of living cells or alloploid•polyploid-nucleate cells can be recognized and sorted in the following manner, without nuclear staining of cells. That is, the inside of a flow cell is irradiated with single mode (SM) light. Then, a signal obtained by allowing a certain region to receive the irradiation light and the light that has transmitted through a cell is analyzed. Alternatively, a signal obtained by combining a signal obtained by allowing a certain region to receive the irradiation light and the light that has transmitted through a cell with a light reception signal originating in side-scattering light is analyzed.

Here, SM light that has transmitted through a flow channel, light that has transmitted through a cell, and light reflected, scattered, and diffracted from the cell are collectively called transmitted light. The SM light is always received at a certain region which functions to receive transmitted light. However, SM light-receiving power changes at the time of cell measurement. The peak, width, area, or the like of a pattern of changes (signal) is called transmitted light information.

Although it is considered that there is a variation in width value (variation in flow velocity) depending on locations where the cell is flowing, it is possible to improve the accuracy by analyzing the transmitted light information having almost the same flow velocity. Specifically, it was found to be able to recognize G1 phase of a cell cycle during which chromosomes of a cell are stable and M phase of a cell cycle during which chromosomes increase in number and a cell nucleus or a cell grows bigger, and thereby to be able to sort cells.

A method of distinguishing and sorting cells according to a first aspect of the invention is a cell distinguishing and sorting method of distinguishing and sorting a specific cell mass or a part of living cells in the cell mass using the use of transmitted light information reflecting either or both of the morphological characteristics of cells such as size and shape and the characteristics of the internal structure of cells such as cytoplasm and nucleus.

A method of distinguishing and sorting cells according to a second aspect of the invention is a cell distinguishing and sorting method of distinguishing and sorting living cells with the use of the transmitted light information, and side-scattering light information that reflects the characteristics of the internal structure of cells.

A method of distinguishing and sorting cells according to a third aspect of the invention is a cell distinguishing and sorting method in which the part of living cells in the specific cell mass is a part of cells at the G1 phase of a cell cycle.

A method of distinguishing and sorting cells according to a fourth aspect of the invention is a cell distinguishing and sorting method in which the part of living cells at the G1 phase of a cell cycle are smaller than the smallest cell at S phase in a histogram of cells where the abscissa axis indicates the transmitted light information or in an analytical dispersion diagram of cells where the abscissa axis indicates the transmitted light information and the vertical axis indicates the side-scattering light information, that is, cells that are present at a left base portion of a curve in the analytical dispersion diagram.

A method of distinguishing and sorting cells according to a fifth aspect of the invention is a cell distinguishing and sorting method in which the part of living cells in the specific cell mass is a part of cells at the M phase of a cell cycle.

A method of distinguishing and sorting cells according to a sixth aspect of the invention is a cell distinguishing and sorting method in which the part of living cells at the M phase of a cell cycles are bigger than the biggest cell at the S phase in a histogram of cells where the abscissa axis indicates the transmitted light information or in an analytical dispersion diagram of cells where the abscissa axis indicates the transmitted light information and the vertical axis indicates the side-scattering light information, that is, cells that are present at a right base portion of a curve in the analytical dispersion diagram.

A method of distinguishing and sorting cells according to a seventh aspect of the invention is a cell distinguishing and sorting method in which, the part of living cells in the specific cell mass sorts the specific cell mass or the part of living cells in the cell mass, regardless of the presence and absence of fluorescent processing such as an antibody•antigen reaction at the cell surface and expression of fluorescent protein in the cell, without performing fluorescent labeling processing for nuclear staining.

A method of distinguishing and sorting cells according to an eighth aspect of the invention, wherein a part of specific cells such as stem cells is distinguished using at least transmitted light information, the specific cells such as stem cells that are bigger than the biggest cell at the S stage in a histogram of cells where an abscissa axis indicates the transmitted light information, or in an analytical dispersion diagram of cells where an abscissa axis indicates the transmitted light information and a vertical axis indicates the side-scattering light information, transmitted light with information, or fluorescence information, are sorted, that means, sorting cells that are present at a right base portion of a curve in the analytical dispersion diagram.

A method of distinguishing and sorting cells according to a ninth aspect of the invention, wherein one cell from the part of living cells in the specific cell mass is sorted in one well.

A method of distinguishing and sorting cells according to a tenth aspect of the invention, wherein, in the transmitted light information of the specific cell mass, cells in a region of 1% from the maximum value are distinguished as alloploid-nucleate cells or polyploid-nucleate cells and sorted.

A method of distinguishing and sorting cells according to an eleventh aspect of the invention, wherein, when a value obtained by subtracting $4\sigma$ from a mean value of the region of 1% is larger than a mean value of the transmitted light information of the specific cell mass, cells are distinguished as alloploid-nucleate cells or polyploid-nucleate cells and sorted.

A method of distinguishing and sorting cells according to a twelfth aspect of the invention, wherein, when a value obtained by subtracting $4\sigma$ from the mean value of the region of 1% is larger than the mean value of the transmitted light information of the specific cell mass and a value (CV) obtained by dividing a standard deviation ($\sigma$) of cells of the 1% by the mean value is equal to or more than 8%, the cells are distinguished as alloploid-nucleate cells or polyploid-nucleate cells and sorted.

A method of distinguishing and sorting cells according to a thirteenth aspect of the invention is a cell distinguishing and sorting method in which the part of living cells in the certain specific cell mass is blood cells that are sorted without fluorescent labeling processing for nuclear staining regardless of the presence and absence of fluorescent processing such as an antibody•antigen reaction at the cell surface or expression of fluorescent protein in the cell. Since the polyploid-nucleate cells or alloploid-nucleate cells that are not supposed to be normally present in blood are distinguished, this method is applicable to cancer diagnosis. For example, a cancer cell is a polyploidy or an alloploidy, each having a number of nuclei in many cases. By determining the number of polyploid-nucleate cells or alloploid-nucleate cells in blood, this method is applicable to a method of predicting prognosis of a cancer and treatment effect on the cancer.

A device for sorting cells according to a first aspect of the invention, an irradiating portion that irradiates a cell with light, a cell measuring portion configured to be able to acquire transmitted light information reflecting at least any one of the morphological characteristics of cells that include size and shape and the characteristics of the internal structures of cells that include nucleus and cytoplasm and to acquire side-scattering light information reflecting the characteristics of the internal structures of cells, an analyzing portion that analyzes the transmitted light information and side-scattering light information that are measured, and a cells sorting portion that distinguishes and sorts living cells part of a specific cell mass or the specific cells mass that is obtained by the analyzing portion.

A device for sorting cells according to a second aspect of the invention, wherein the cell sorting portion has a function of sorting a single or a plurality of living cells in a predetermined region in a histogram of cells where an abscissa axis indicates the transmitted light information or an analytical dispersion diagram of cells where an abscissa axis indicates the transmitted light information and a vertical axis indicates the side-scattering light information, into predetermined wells.

Effects of the Invention

According to the invention, the inside of a flow cell is irradiated with single mode (SM) light, and a signal obtained by causing a certain region to receive the irradiation light and the light that has transmitted through a cell is analyzed. Alternatively, the inside of a flow cell is irradiated with single mode (SM) light, and a signal obtained by causing a certain region to receive the irradiation light and the light that has transmitted through a cell and a light-receiving signal originating in side-scattering light are combined to be analyzed. Accordingly, it is possible to distinguish a cell cycle of living cells and sort the living cells without nuclear staining of cells.

Without staining cells, only cells at the G1 and M phases of a cell cycle, polyploid-nucleate cells, or alloploid-nucleate cells can be separated from other cells and sorted as being alive. Accordingly, the invention may contribute to study on cells, and in particular, study on inducing differentiation of cells. In addition, since the living cells that have been sorted once can be resorted in response to the change of the living cells, the invention may contribute to real-time study on cells. Furthermore, since the stem cells•cancer stem cells can be extracted without using fluorescent chemicals, excessive damages to cells may be avoided, which contributes to inducing differentiation of cells.

EXPLANATION OF LETTERS AND NUMBERS

Figure 1:
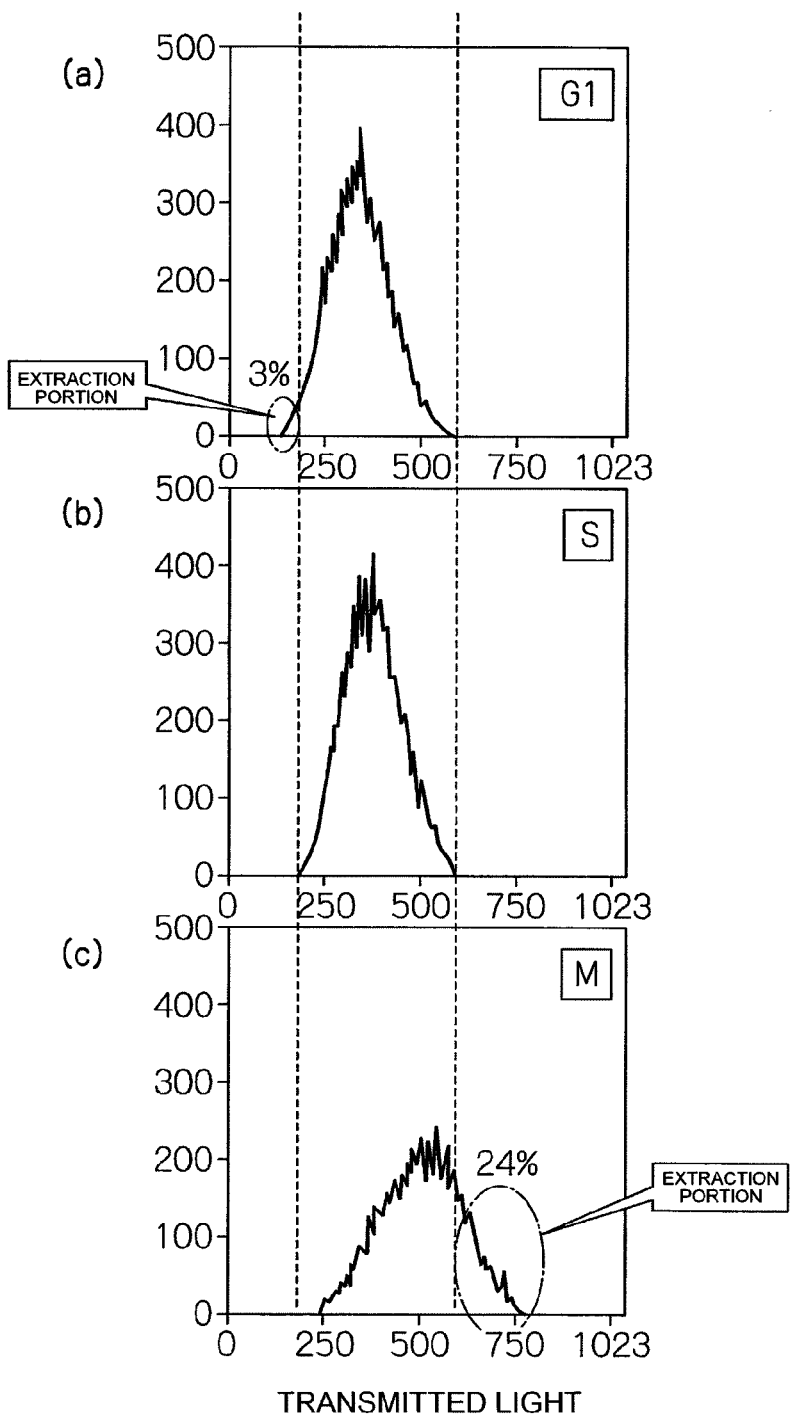
FIG. 1 is a histogram where the abscissa axis indicates the peak of transmission light information, which is produced by detecting the transmitted light information according to the invention.

1: Flow cell
2: Sample flow
3: Sheath flow
4: Optical connector
5: Laser
6: Cell
7: Transmitted light receiving device
8: Optical fiber
9: Side-scattering light receiving device
10: Fluorescence device

BEST MODE FOR CARRYING OUT THE INVENTION

A method and device for sorting cells according to the invention will be described with reference to the accompanying drawings.

One exemplary embodiment of a method and device for distinguishing and sorting cells according to the invention relates to a method of distinguishing and sorting a specific cell mass or a part of living cells in the specific cell mass with the use of transmitted light information reflecting the morphological characteristics of cells such as size and shape which can be obtained by irradiating cells with light, or both of transmitted light information reflecting the morphological characteristics of cells such as size and shape which can be obtained by irradiating cells with light and side-scattering light information reflecting the characteristics of the internal structure of cells. The part of living cells in the specific cell mass is a part of cells at G1 phase or M phase of a cell cycle.

The period of mitosis is called M phase. In most of cells, it ends within an hour and is just an extremely brief time in the entire cell cycle. The period from the M phase of a previous cell cycle to the M phase of a new cell cycle is called interphase during which cells grow, synthesizing necessary materials. Most of protein and other materials are being continuously synthesized all the while during the interphase. The interphase can be further divided into G1, S, and G2 phases. During the S phase, DNA replication occurs. The period from the end of the M phase until the beginning of the S phase is called G1 phase, which is the first gap phase. In cells that keep dividing, enzymes required for DNA synthesis are activated during the G1 phase, and the cells can normally enter the S phase through the activation. Cells that have stopped dividing cannot enter the S phase, leaves the cell cycle, and stays at a state of G0 phase similar to G1 phase. After completion of the S phase, the cells enter the second gap phase, G2, during which the final preparation stage for cell division begins and protein synthesis is accelerated.

The M phase is broken down into prophase, metaphase, anaphase, and telophase. During the prophase, chromosomes condense and can be observed under a microscope. At the initiation of the metaphase, a nuclear membrane disappears and the chromosomes are aligned in a line on the cell equator. During this phase, formation of spindle is completed. During the anaphase, sister chromatids that have been joined near centromere are separated in a way that they are pulled by the spindle, and start to migrate toward the poles. During the telophase, the condensed chromosomes are disintegrated and the nuclear membrane is formed again. From this phase, cytokinesis starts and cell division terminates.

In the method of distinguishing and sorting cells according to the invention, as described above, the S phase is the phase for proliferation and recovery of chromosomes, and is unstable. Accordingly, the method recognizes the G1 phase and the M phase during which chromosomes are stable to sort cells.

Figure 7:
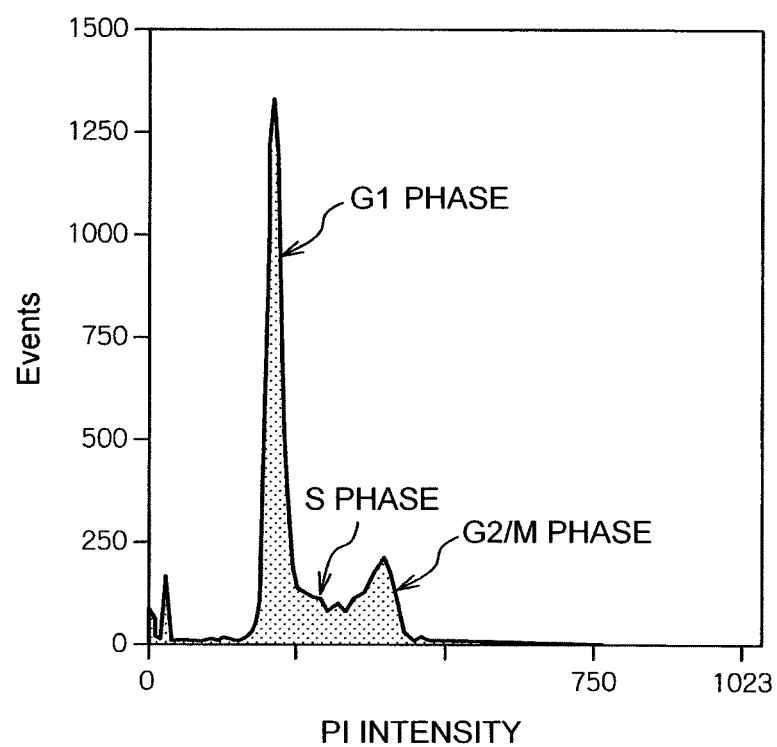
FIG. 7 is a diagram illustrating an analysis result of a cell cycle based on nuclear staining (PI) of cells.
Figure 8:
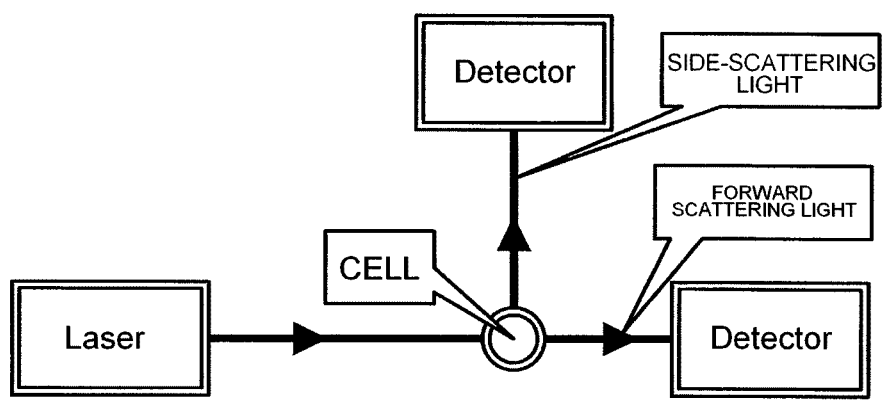
FIG. 8 is a diagram illustrating measurement analysis of scattering light that is obtained using a conventional flow cytometer.

The transmitted light reflects the morphological characteristics of cells such as size and shape as information. The side-scattering light reflects the characteristics of the internal structure of cells as information. By using the transmitted light or using the above two kinds of information in combination, a specific phase of a cell cycle is recognized. Conventionally, as shown in FIG. 7, analysis of the cell cycle is performed through nuclear staining (PI staining) of cells. As a result, as shown in FIG. 7, the G1 phase, S phase, and M phase are clearly recognized. However, cells are damaged from the nuclear staining of cells and come to perish, so that the nuclear staining of cells cannot be applied to living cells (A certain kind of nuclear staining causes damages to cells but does not make the cells perish).

Figure 4:
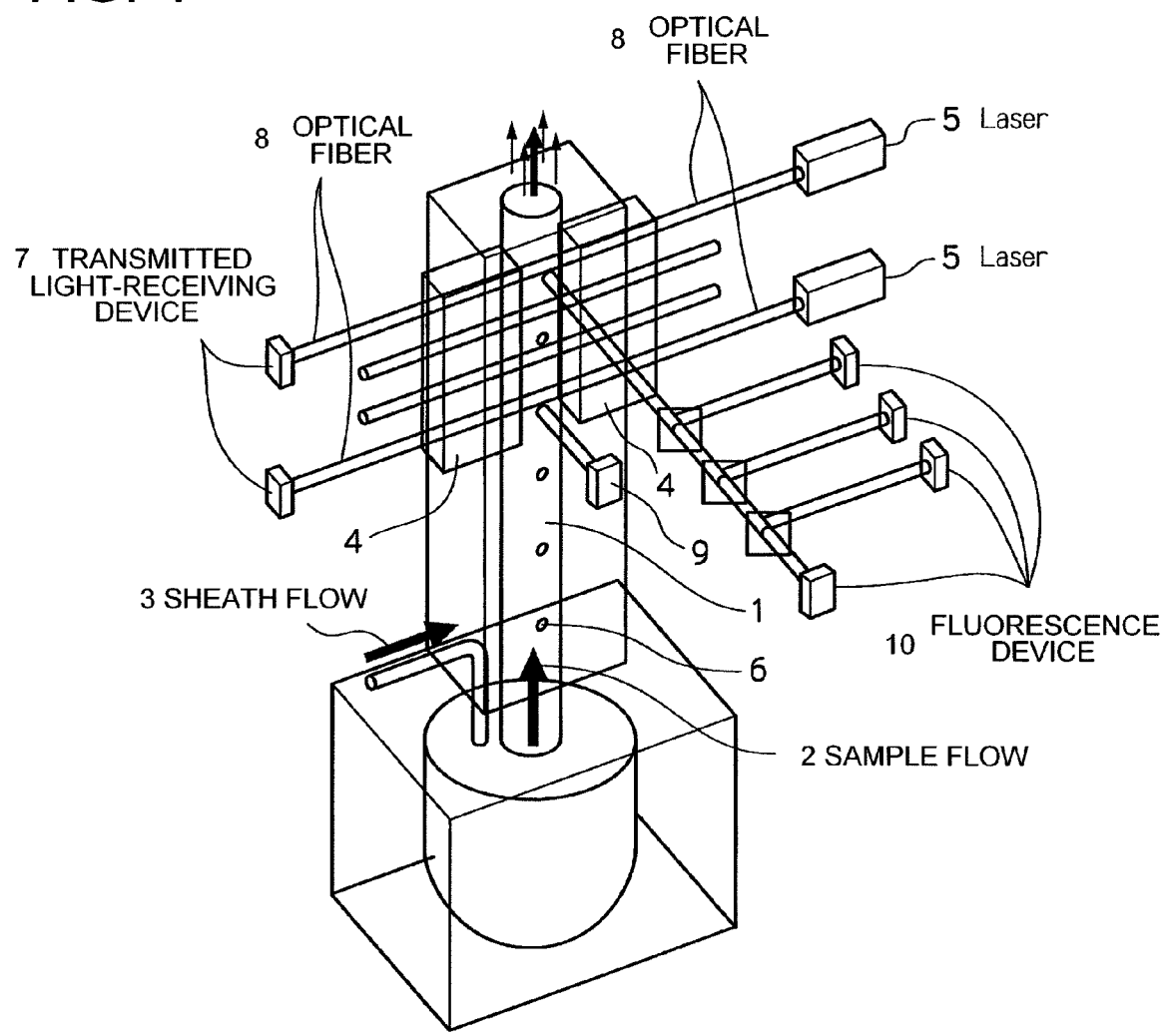
FIG. 4 is a diagram illustrating the measurement principle of a device for sorting cells according to the invention.

FIG. 4 is a diagram illustrating the measurement principle of a cell distinguishing and sorting method according to the invention. In a flow cell 1, a laminar flow composed of a sample (cell) suspension flow 2 and a sheath liquid flow 3 is formed. The sheath liquid and the sample liquid are forced out by the pressure from a compressor or the like. At this time, if the pressure of the sample liquid is made to be lower than the pressure of the sheath liquid, the sample liquid flow is hydrodynamically narrowed at the stage of forming the laminar flow by meeting with the sheath liquid and the flow diameter of the sample flow surrounded by the sheath flow becomes thinner. As a result, cells are arranged in a line. As such, adjusting a difference in pressure makes individual cells stand in a line, so that cells enter a stage in which cells flow into the flow cell one after another.

A pair of connectors 4 (for example, multiconductor connector 4) is disposed to pinch the flow cell 1 from the both sides to narrow the flow cell 1. A laser 5 and an optical fiber 8 are arranged and fixed so that light from the laser 5 is irradiated onto a cell 6 that flows to pass through the flow cell 1 and the transmitted light that has transmitted through the cell 6 is received by a transmitted light-receiving device 7. That is, SM light that is delivered from the laser 5 via a single mode (SM) optical fiber 8 is irradiated onto the flow cell 1. As described above, the cells flow in turns one after another in a manner of crossing the SM light. An end of the optical fiber 8 and the laser 5 are connected. The other end is provided with the transmitted light-receiving device 7. Parameters of the transmitted light information include a peak value of the transmitted light information, a width value of the transmitted light information, and an area value of the transmitted light information.

Furthermore, when the cell 6 is exposed to laser light while it is in the flow cell 1, the cell 6 scatters the laser light (in the case of fluorescence-labeled, fluorescence is expressed from a fluorescent pigment). A side-scattering light-receiving device 9 for detecting the side-scattering light (SSC) that scatters at an angle of 90° to the laser light, among the light components scattering from the cell 6, is provided. In addition, a fluorescence device 10 for splitting light and detecting a wavelength component using an optical filter is disposed in a direction of an angle of 90° like the side-scattering light (SSC).

The sample suspension liquid and the sheath liquid that have passed through the flow cell, form liquid droplets which are sorted in predetermined wells. In the figure, the sheath liquid and the sample liquid flow upward. However, they may flow downward. In normal cases, the liquids flow downward. When a plurality of excited wavelengths is required, or a specific wavelength is required, a plurality of lasers is mounted and can be selectively used according to the purposes. In addition, a measuring portion for measuring the flow velocity of the sample liquid is further provided.

The light-receiving device produces a current when it receives light, and the current is converted to a voltage pulse for pulse processing. The voltage pulse is A/D-converted (a voltage pulse is an analog value. When the analog value is measured with an indicator with 1024 scales, it is changed to an integer from 0 to 1023. This is called analog/digital conversion (A/D conversion)). By using data of values of parameters, various kinds of histograms are produced by a computer (analysis software). FIG. 1 is a histogram that is produced by detecting the transmitted light information according to the invention.

Figure 9:
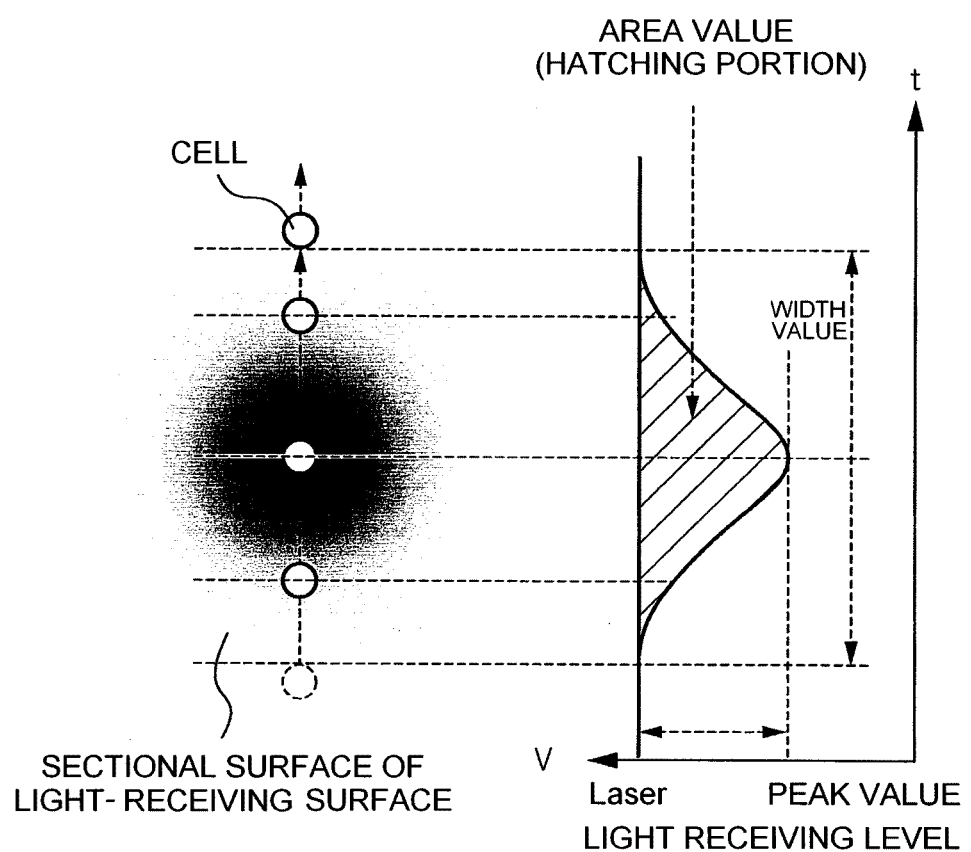
FIG. 9 is a conceptual diagram illustrating a peak value, a width value, and an area value as parameters of the transmitted light information.

Regarding the above-described transmitted light information, FIG. 9 illustrates the conceptual diagram. FIG. 9 shows the peak value, the width value, and the area value as parameters of the transmitted light information. The transmitted light-receiving region receives the single mode (SM) light all the time and has a certain light-receiving power. When the cell passes, the light-receiving level (power) changes in a fashion of a quadratic curve illustrated in the figure. In the case of the same width value, the cell with a higher peak value exhibits lower transmittance with respect to the transmitted light. This means that the cell has a larger nucleus (the transmittance of the cell nucleus is lower than that of the cytoplasm).

In FIG. 1, the abscissa axis indicates the peak in the transmitted light information and the vertical axis indicates frequencies. The more right side in the abscissa axis represents the bigger sample (cell) size and the more left side in the abscissa axis represents the smaller sample (cell) size.

First, if the cell is irradiated with laser light and the transmitted light is detected and analyzed, the size of the cell for each phase of the cell cycle of the cell division is manifested. Actually, the size changes while the cell undergoes the cell division, from the G1 phase which is a relatively stable stage of a cell cycle to the M phase during which chromosomes increase in number and cells or cell nuclei increase in size, through the S phase which is the transition period. FIG. 1 clearly illustrates the change in size of cells. That is, the sizes of cells at individual phases are in the following relationship and comply with substantial cells.

$$G1 < S < G2/M$$

Next, when the curve of the G1 phase that is a relatively stable phase is examined with the use of the curve of the S phase of a cycle of cell division shown at the center of FIG. 1 as reference, in the G phase, it can be found that a left base portion of the curve spreads out further toward the left side as compared from the left side of the S phase. Accordingly, if the left base portion (accounting for about 3% of the entire region) of the curve that protrudes toward the left side at the G1 phase is sorted, only living cells at the G1 phase surely can be sorted out from other cells.

In a similar manner, when the curve of the M phase during which chromosomes increase in number and cells or cell nuclei increase in size is examined using the curve of the S phase of a cycle of cell division as reference, it can be found that a right base portion of the curve spreads out further toward the right side from the right end portion of the S phase. Accordingly, if the right base portion (accounting for about 24% of the entire region) that protrudes toward the right side at the M phase is sorted, only living cells at the M phase are surely sorted out from other cells.

According to the invention, since living cells are sorted, the sorted cells keep repeating cell division and thus exhibit, over time, respective phases of the G1, S, and M phases having the feature illustrated in FIG. 1. Furthermore, all regions of respective phases that can be recognized can be sorted (for example, not only the left base portion of the G1 phase but also the entire region can be sorted).

Figure 6:
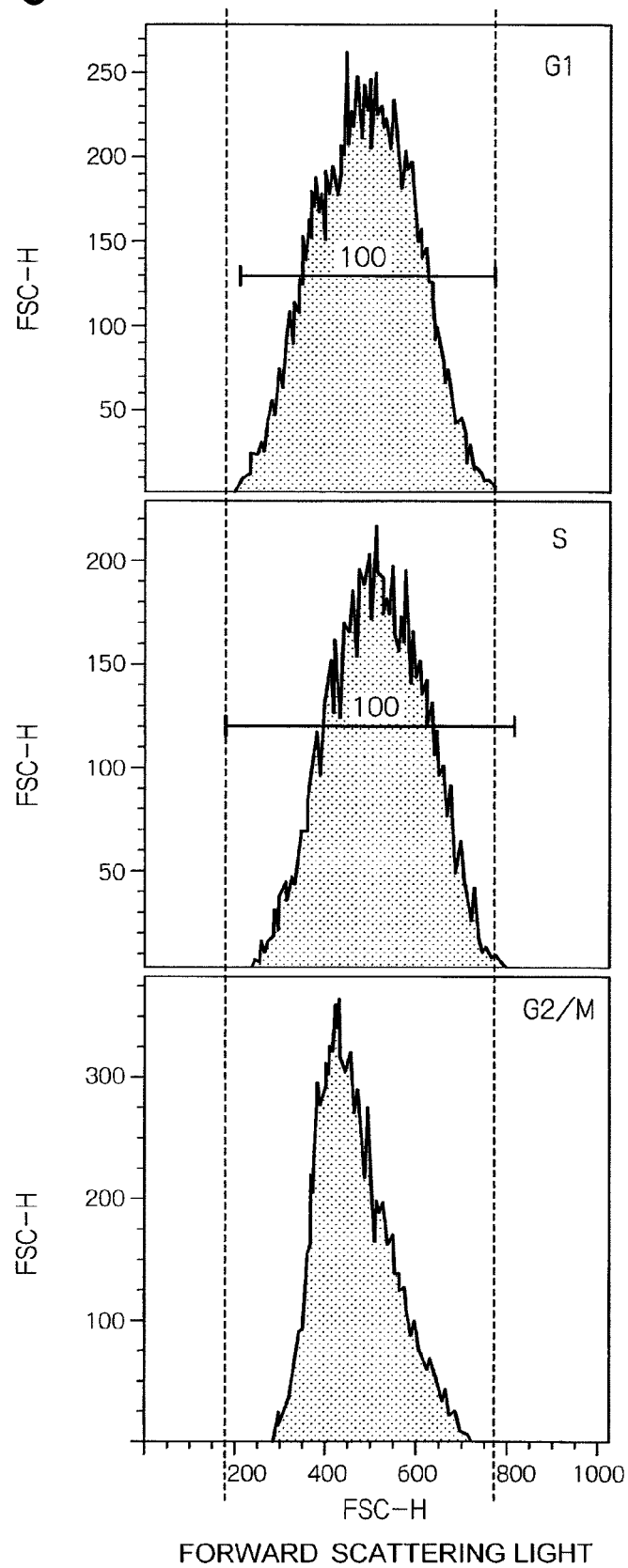
FIG. 6 is a histogram of forward scattering light information according to a related art, in which the abscissa axis indicates the peak of the forward scattering light information.

FIG. 6 illustrates a histogram of forward scattering light information according to a conventional art. The abscissa axis indicates the peak of the forward scatter in the forward scattering light information. As shown in FIG. 6, according to the conventional forward scattering light information, the relationship in size among G1, S, and M phases is unclear. Accordingly, living cells cannot be sorted for each phase.

Figure 2:
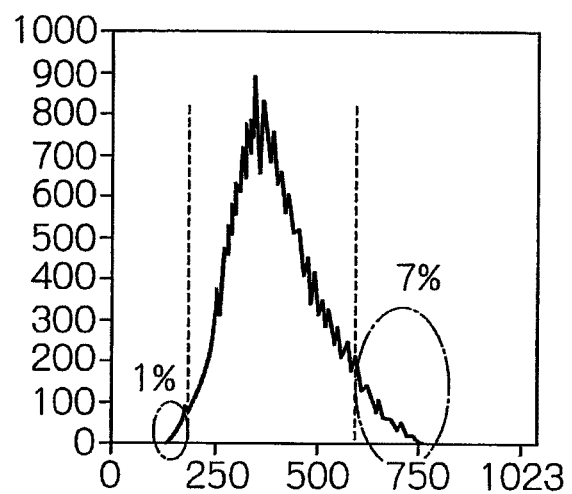
FIG. 2 is a histogram where the abscissa axis indicates the peak of transmitted light information, which is produced by detecting transmitted light information on HeLa cells for all phases of a cell cycle.

FIG. 2 illustrates a histogram of transmitted light information for the entire cell cycle of HeLa cells. The abscissa axis indicates the peak of the transmitted light information. The boundary line illustrated by a dotted line of FIG. 2 is similar to the boundary line of FIG. 1. Even for the transmitted light information of the entire cell cycle of cells, the left base portion of the curve represents the G1 phase and the right base portion represents the M phase. Accordingly, if the left base portion (accounting for about 1% of the entire region) that protrudes toward the left side of the G1 phase is sorted, only living cells at the G1 phase can be sorted out from other cells, and if the right base portion (accounting for about 7% of the entire region) that protrudes toward the right side of the M phase is sorted, only living cells at the M phase can be surely sorted out from other cells.

Figure 3:
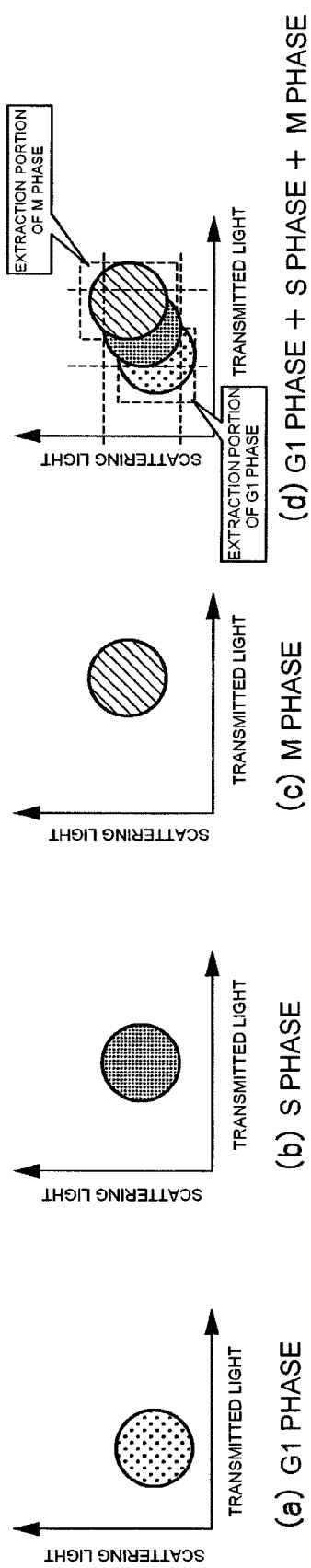
FIG. 3 is an image diagram in which transmitted light information and side-scattering light information are shown in a dot-plotted form.

FIG. 3 is an image diagram illustrating a dot-plotted state of the transmitted light information and the side-scattering light information. The vertical axis indicates the side-scattering light information and the abscissa axis indicates the transmitted light information. The more right side on the abscissa axis represents the larger size in cell shape. FIGS. 3(a), 3(b), and 3(c) illustrate information of G1 phase, S phase, and M phase, respectively. As shown in the figures, the size increases through the respective phases of the G1, S, and M phases gradually. FIG. 3(d) illustrates information in which G1, S, and M phases are superimposed. The boundary line illustrated by a dotted line of FIG. 3(d) corresponds to the size of the S phase. As shown in the figure, even in the dot-plotted state of the transmitted light information and the side-scattering light information, the left base portion represents the G1 phase and the right base portion represents the M phase.

Without performing staining process for staining cells with fluorescent pigments, such as an antibody•antigen reaction, specific cells such as stem cells are distinguished with the use of the transmitted light information. As for the specific cell such as a stem cell, since most of the internal structure of the cell is a nucleus, such a cell exhibits transmittance lower than those of general cells and thus a signal of the transmitted light is strong (high) (because it is a damping signal). Similar to the above description, if a histogram is produced based on the transmitted light information, a region of specific cells such as stem cells corresponds to a region of the right base portion of a curve. Similarly, even for specific cells such as stem cells, an analytical dispersion diagram may be produced by a combination of the transmitted light and other light information such as scattering light. The specific cells in the region of the above-described right base portion are sorted. For this instance, the specific cells are cells such as stem cells having self-replication ability and pluripotency or cancer stem cells, or cancer cells that become polyploid nuclei. The cancer cells are polyploid nuclei having a number of nuclei in many cases. Consequently, in the cancer cell, the ratio of the nucleus to the entire cell is large, which leads to the characteristic of low transmittance. Therefore, the cancer cells are similar to the stem cells.

In addition, the invention can be applied to distinguishing and sorting of polyploid-nucleate cells, alloploid-nucleate cells. That is, distinguishing and sorting of polyploid-nucleate cells or alloploid-nucleate cells are performed with the use of transmitted light information. During the cytokinesis that follows the division of chromosomes, each of cells that have failed to divide their cytoplasms in half comes to have nuclei which are double in number as compared with general cells (or have a nucleus with chromosomes that are double in number). Among such cells, there are abnormal cells with various types of abnormalities such as cells with an abnormal number of chromosomes even if they have survived. These are referred to as polyploid-nucleate cells or alloploid-nucleate cells. The measurement result of nuclear-stained HeLa cells is analyzed, and it was found that a region ranging from the center of the G2/M region to $3\sigma$ ($\sigma$ is the standard deviation) was a region of polyploid-nucleate cells•alloploid-nucleate cells. Based on the result, it was found that the region of polyploid-nucleate cells•alloploid-nucleate cells was a region of top 1% in a histogram of FIG. 14 where the abscissa axis indicates the peak in the transmitted light information, that is, a region of top 1% in terms of cell size (a right end portion of FIG. 14, R3 region). According to the invention, based on the transmitted light information, if the cells in the region of top 1% in the histogram showing the peak in the transmitted light information are sorted, polyploid-nucleate cells, alloploid-nucleate cells can be sorted out from other cells with high accuracy.

In addition, when a value obtained by subtracting $4\sigma$ from the mean value of the region of top 1% in the histogram showing the peak in the transmitted light information is larger than the mean value of the peaks in the transmitted light information of the HeLa cells, the cells of the 1% region are polyploid-nucleate cells or alloploid-nucleate cells. This means that the mean value of the entire region is at a distance of 4σ from the mean value of the top 1%. On the other hand, when a value obtained by subtracting 4σ from the mean value of the region of the top 1% in the histogram showing the peak in the transmitted light information is larger than the mean value of the entire region and a value (CV) obtained by dividing the standard deviation σ of the top 1% cells by the mean value is equal to or more than 8%, the above-described 1% cells are polyploid-nucleate cells or alloploid-nucleate cells. That is, as the value (CV) obtained by dividing the standard deviation σ of the 1% cells by the mean value is set to be equal to or more than a predetermined value, the accuracy is increased.

As described above, based on the transmitted light information, polyploid-nucleate cells or alloploid-nucleate cells can be sorted out alive from other cells without nuclear staining. This may contribute to study on cells, and particularly study on inducing differentiation of cells. In this way, polyploid-nucleate cells or alloploid-nucleate cells that are not supposed to be present in blood are distinguished, and thus it can be applied to cancer diagnosis. For example, in many cases, cancer cells are polyploidy with many nuclei or alloploidy. Since the number of polyploid-nucleate or alloploid-nucleate cells is determined, this method can be applied to a method of predicting prognosis of a cancer and treatment effect on the cancer.

Figure 5:
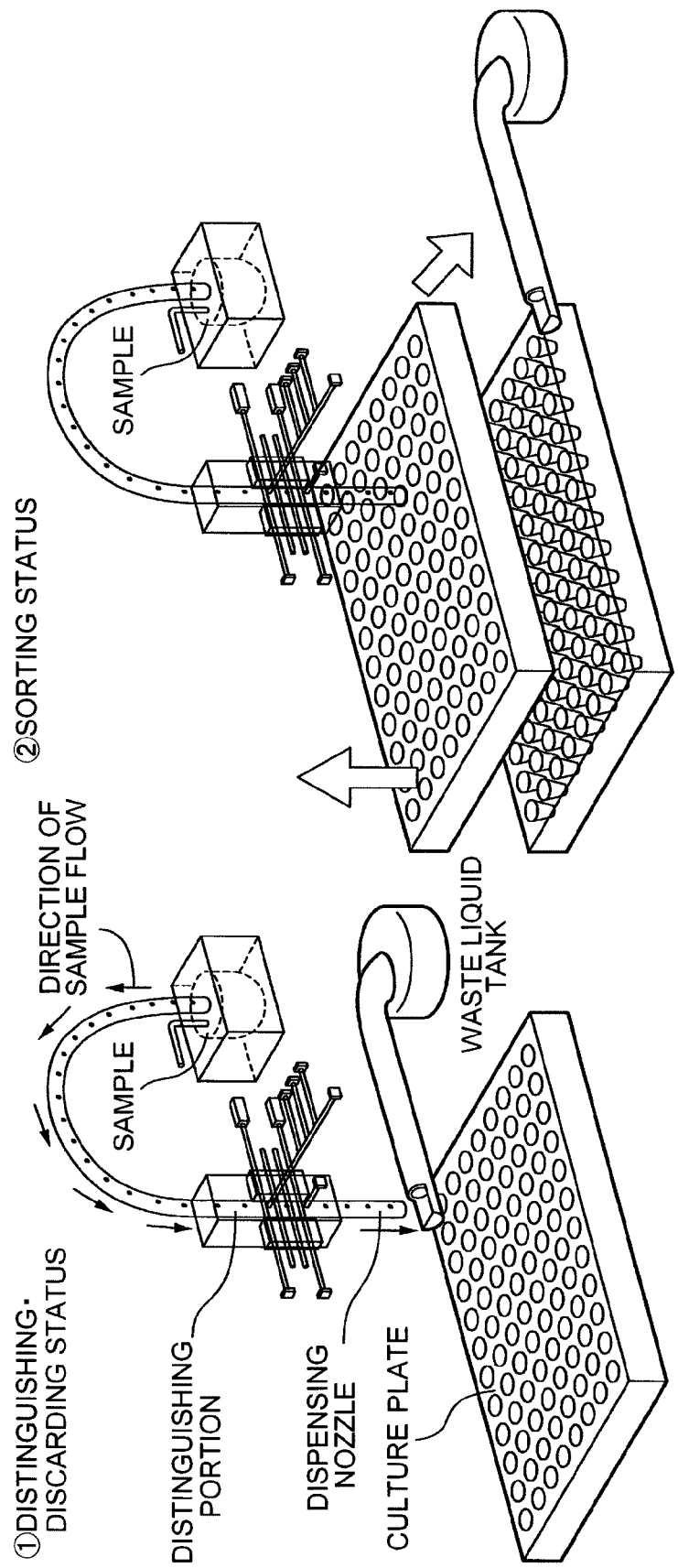
FIG. 5 is a diagram illustrating the structure of a sorting portion.

FIG. 5 is a diagram illustrating the structure of a sorting portion. The sorting portion performs distinguishing, discarding, and sorting. Each of the statuses will be described. That is, operations are different between the status before detection of target cells and the status after detection of the target cells.

(1) Distinguishing and Discarding Statuses

As shown in FIG. 5, a sample liquid continuously flows in a direction of an arrow, laser light is irradiated onto a cell that passes through a flow cell in the distinguishing portion, and it is determined whether or not the cell is a target cell on the basis of the transmitted light information or both the transmitted light information and the side-scattering light information. Until the target cell is detected, a dispensing nozzle is inserted in a waste liquid tank so that non-target cells are discarded into the waste liquid tank.

(2) Sorting Status

When the target cell is detected on the basis of the transmitted light information or both the transmitted light information and the side-scattering light information, time until the target cell arrives at the leading end of the dispensing nozzle is calculated. At the timing in which the cell arrives at the leading end of the nozzle, at the calculated arrival time, the waste liquid tank is taken off and a stage (culture plate) is lifted. In this manner, the leading end of the dispensing nozzle is inserted into individual wells and the target cells are dispensed.

The method of calculating the time until the cell arrives at the leading end of the nozzle is as follows. A plurality of optical signal detecting portions (optical fibers) is arranged in a traveling direction of a sample at sub-micron intervals (the interval of detecting portions has been already known). The flow velocity is calculated from the interval between the respective detecting portions and a difference in time that the cell passes through the respective measuring portions. Since the distance from the detecting portion to the leading end of the nozzle is known, the time until the target cell arrives at the leading end of the nozzle can be calculated.

A cell sorting method according to the invention will be described with reference to Examples.

EXAMPLE 1

A cell sorting device that can sort cells according to the measurement principle shown in FIG. 4 was used. Laser light was irradiated onto a HeLa cell that was passing through the flow cell. The light that had transmitted through the cell or both the light that had transmitted through the cell and the light that have scattered sideways due to the cell were detected, and a histogram was produced using the peak in the transmitted light information. FIG. 1 illustrates the histogram based on the transmitted light information. As shown in FIG. 1, G1 phase, S phase, and M phase of the HeLa cell were measured and analyzed as in FIG. 1a, FIG. 1b, and FIG. 1c, respectively.

The peak in the transmitted light information indicated by the abscissa axis of FIG. 1 reflects the morphological characteristics of cells. On the abscissa axis, the more right side represents a larger size and the more left side indicates a smaller size. The vertical boundary line illustrated by a dotted line corresponds to the size of cells at the S phase on the whole. As shown in FIG. 1, in the case of the G1 phase illustrated in FIG. 1a, the base portion further spreads out at the left side as compared with the S phase of FIG. 1b. Accordingly, as known from the comparison with the S phase of FIG. 1b, the left base portion (accounting for about 3% of the entire region) of FIG. 1 is surely the HeLa cells at the G1 phase and FIG. 1a surely specifies the G1 phase of the cell cycle.

FIG. 2 is the histogram illustrating the peak in the transmitted light information (for all phases of the entire cell cycle) of the HeLa cells. The left base portion on the abscissa axis (accounting for about 3%, 1% of the entire region) illustrated in FIG. 1 and FIG. 2 are gated, and one to plural cells are sorted in predetermined wells. As a result, only cells at the G1 phase during which cells are relatively stable could be sorted. This manner enables only living cells at the G1 phase to be sorted and can significantly contribute to study on differentiation and culture of cells.

EXAMPLE 2

Similarly, a cell sorting device that can sort cells according to the measurement principle shown in FIG. 4 was used. Laser light was irradiated onto a HeLa cell that was passing through the flow cell. The light that had transmitted through the cell and the light that had scattered sideways due to the cell were detected and an analytical dispersion diagram was produced on the basis of transmitted light information and side-scattering light information. FIG. 3 is an image diagram. As shown in FIG. 3, G1 phase, S phase, and M phase of the HeLa cell were measured and analyzed as shown in FIG. 3a, FIG. 3b, and FIG. 3c, respectively.

The transmitted light information indicated by the abscissa axis of FIG. 3 reflects information of the morphology of cells and the side-scattering information indicated by the vertical axis reflects information of the internal structure of cells. On the abscissa axis, the more right side represents a larger size in shape and the more left side indicates a smaller size in shape. The boundary line of FIG. 3(d) that is illustrated by a dotted line corresponds to the size of cells at the S phase on the whole. As shown in FIG. 3(d), in the case of M phase, the right side protrudes from the right end portion of the S phase (corresponding to the right base portion of the histogram). Accordingly, the right-side protruding portion of the M phase that protrudes as compared with the S phase surely means the HeLa cells at the M phase and thus the M phase of the cell cycle is specified.

The right-side protruding portion on the abscissa axis of FIG. 3 is gated, and one to plural cells are sorted in predetermined wells. As a result, only the M phase during which cells are relatively stable among cell dividing phases can be sorted out. Accordingly, only living cells at the M phase can be sorted. This can contribute to study on differentiation and culture of cells.

EXAMPLE 3

FIG. 4 illustrates the structure of the measuring portion that can measure the transmitted light information and the side-scattering light information. By using the cell sorting device incorporating the measuring portion, fluorescence information, transmitted light information, and side-scattering light information of cells can be measured at the measuring points disposed in the traveling direction of cells, and flow velocity information of cells can be measured based on the transmitted light information at a plurality of measuring points.

FIG. 5 illustrates the structure of the sorting portion in which one to plural cells in a predetermined cell group can be sorted in predetermined wells. With the use of the cell sorting device incorporating the sorting portion, cells to be sorted, that is, target cells at all phases can be sorted by transporting the dispensing nozzle to the predetermined wells from the waste liquid tank at proper timing since traveling time of cells to the dispensing nozzle can be learned from the velocity information.

EXAMPLE 4

Cells at the G1 phase and the M phase that were sorted in Example 1 and Example 2 were cultured under predetermined conditions and then analysis like Example 1 or Example 2 was performed again to sort the cells. As a result, a result similar to the results of Example 1 and Example 2 was obtained.

EXAMPLE 5

Figure 10:
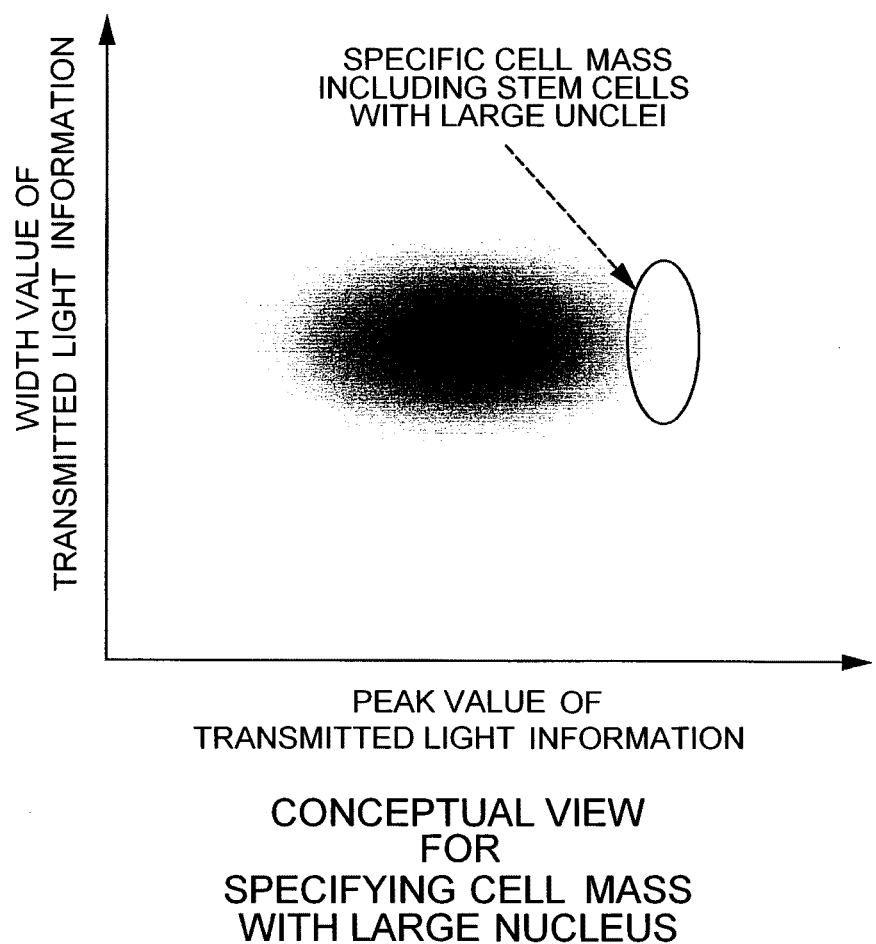
FIG. 10 is a conceptual diagram illustrating a method of specifying specific cells such as stem cells that are specified using the peak value of transmitted light information, and the width value of transmitted light information that is within a predetermined range in flow velocity.

FIG. 10 is a conceptual diagram illustrating a method of specifying specific cells such as stem cells specified on the basis of the peak values of the transmitted light information and the width values of the transmitted light information within a determined velocity range. The width values of the transmitted light information that falls within the determined flow velocity range mean that the cells have almost the same size. In cells in a region of a higher peak value in the transmitted light information, the information reflects the characteristics of nuclei having lower transmittance than that of cytoplasm. That is, when the cells have the same size, as the nuclei of cells become larger in size, the peak value in the transmitted light information becomes higher. In such a case, there is a strong possibility that the cells are specific cells such as stem cells. Regarding the flow velocity, it varies depending on position to position in the sectional surface of the light-receiving surface through which the cell passes as shown in FIG. 9. Accordingly, if cells have the same flow velocity, the cells are passing through almost the same position on the sectional surface of the light-receiving surface.

Stem cells or cancer stem cells have the feature that the size of nuclei thereof is almost two times the size of those of general cells. Accordingly, the conventional feature that cells emit fluorescent chemicals (Hoechst33342) from their bodies is utilized. However, use of such feature is problematic when considering the influence of the fluorescent chemicals on cells and the accuracy of sorting. According to the present exemplary embodiment, by using the unique characteristic of stem cells•cancer stem cells, that is, the characteristic of having a large nucleus, that is, using the right side (large value) of the histogram where the abscissa axis indicates the transmitted light information or the right side (large value) of the peak value of the transmitted light information indicated by the abscissa axis, using the width value of the transmitted light information indicated by the vertical axis, or using the analytical dispersion diagram of side-scattering light information reflecting information of the morphology and the internal structure of cells, a cell mass having a larger value in the transmitted light information is specified and sorted. Thereby, candidates of stem cells or cancer stem cells are extracted.

Figure 11:
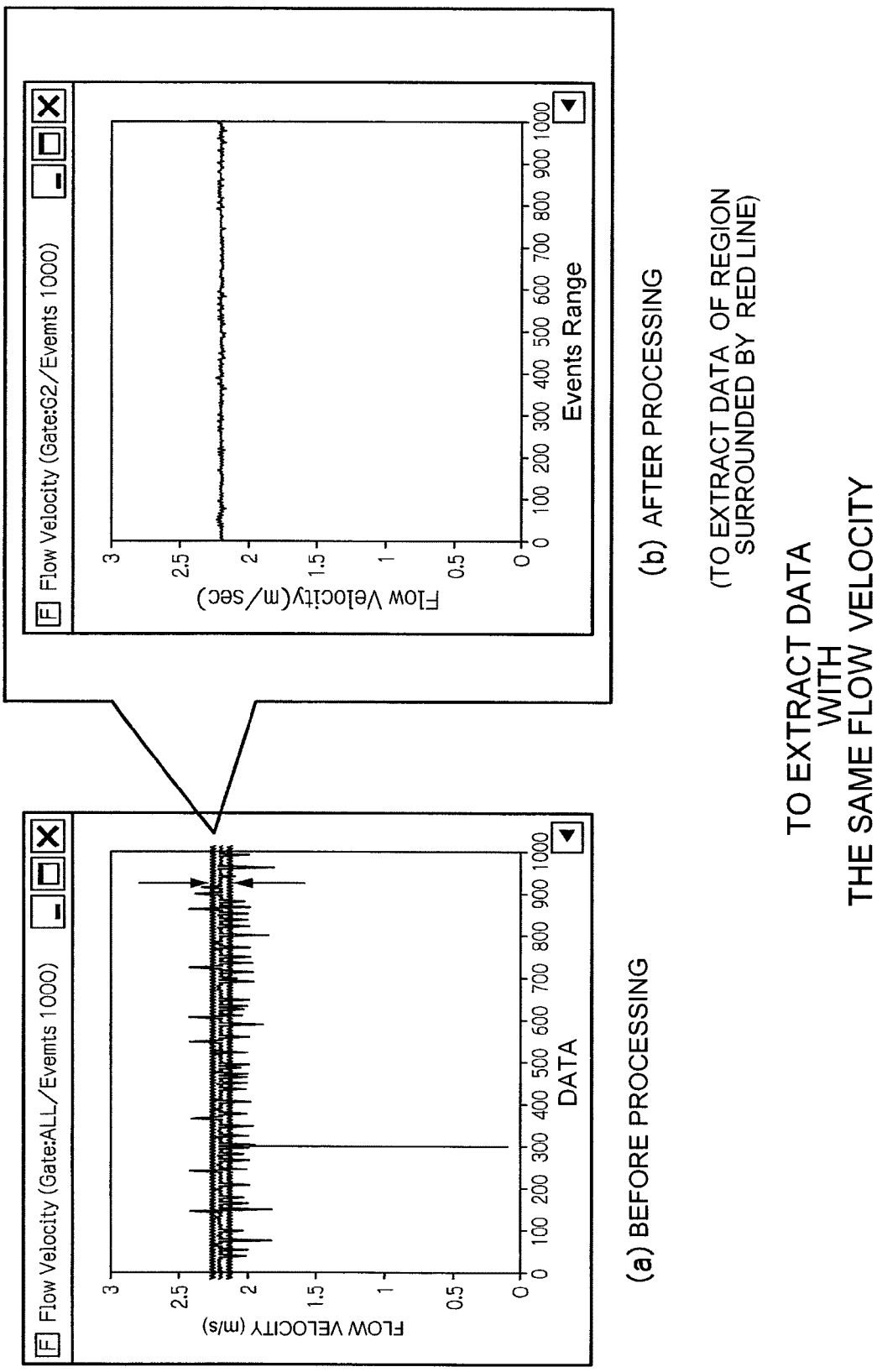
FIG. 11 illustrates an analysis result obtained after extracting data with almost the same flow velocity.

In this case, variation in width value (variation in flow velocity) depending on position which the cell is passing through can be considered. However, by extracting and analyzing data with almost the same flow velocity, as illustrated in FIG. 11, the accuracy is improved.

EXAMPLE 6

By measuring the nuclear-stained HeLa cells, it was found that almost half of the cells in a region of top 1% from the maximum value (that is, the right end portion of the histogram of the peak in the transmitted light information illustrated in FIG. 2) of the transmitted light information (peak of the transmitted light information) were alloploid•polyploid-nucleate cells in the following manner. That is, based on the correlation between the result obtained by measuring nuclear-stained HeLa cells and distinguishing performed on the basis of the transmitted light information, and based on the transmitted light information, it is confirmed that distinguishing and sorting with high accuracy is enabled as follows.

Figure 12:
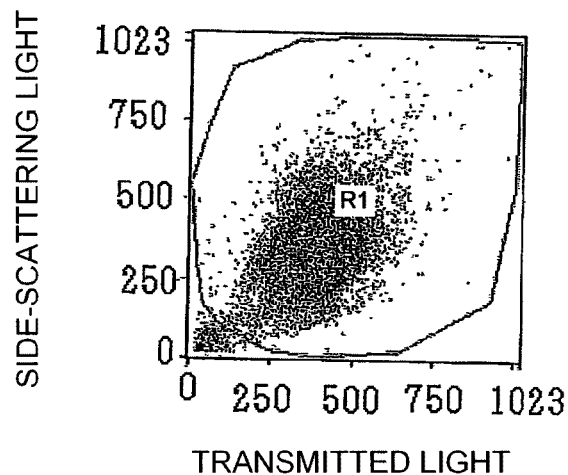
FIG. 12 is a dot-plotted graph where the abscissa axis indicates the peak of transmitted light in the transmitted light information and the vertical axis indicates the peak of transmitted light in the side-scattering light information.

First, nuclear-stained HeLa cells were measured with a flow cytometer of FIG. 5. FIG. 12 illustrates a dot-plotted graph where the abscissa axis indicates the peak of the transmitted light information and the vertical axis indicates the peak of the side-scattering light. The transmitted light reflects the size of cells. That is, as the cell size becomes larger, the larger value can be obtained. The side-scattering light reflects the internal structure of cells. That is, as the internal structure becomes more complicated (the nuclei are bigger in size or larger in number), the larger value can be obtained. In FIG. 12, the left lower portion is excluded as noise information (cell fragments or the like). The remaining region other than the noise information is referred to as a region R1.

This technique is premised on the measurement of a single cell mass. However, when coagulation of cells is considered or intrusion of cell fragments that are finer than the cells to be measured is considered, a process of verifying a signal width of transmitted light•scattering light signal may be included. In the case in which the value of the signal width is outside a range of $2\sigma$ from the mean value, it is speculated that a plurality of cells is coagulated or cell fragments are present, and there is a possibility that a signal from a single cell cannot be analyzed. Accordingly, data that is outside the range of $2\sigma$ from the mean value is excluded, and the accuracy of analysis is increased.

Figure 13:
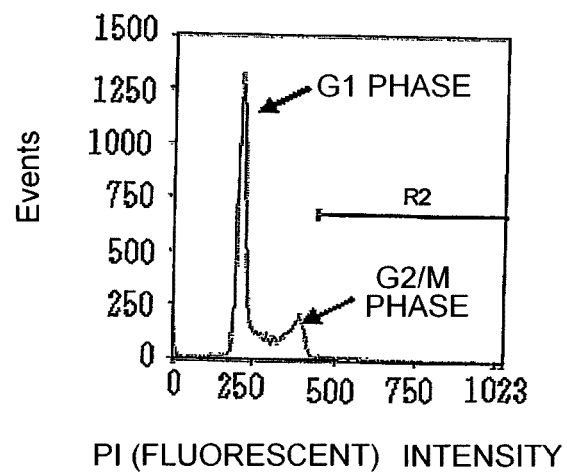
FIG. 13 is a histogram for a region R1 of FIG. 12, where the abscissa axis indicates fluorescent intensity of a cell nucleus.

Next, regarding the above-described region R1, FIG. 13 illustrates a histogram where the abscissa axis indicates the fluorescent intensity of a cell nucleus. The larger peak represents the fluorescent intensity of a cell nucleus at the G1 phase. The smaller peak represents the fluorescent intensity of a cell nucleus at the G1/M phase. It is considered that a region having a peak larger than the peak of the G2/M phase represents a region of alloploid•polyploid-nucleate cells. A region having a peak larger than that of the G2/M phase is defined to be at a distance of 3$\sigma$ or more from the center of the G2/M region. This region is called R2. Examining the number of data in the R2 region, the result was 205 data (that is, accounting for 1.34% of the entire region).

Figure 14:
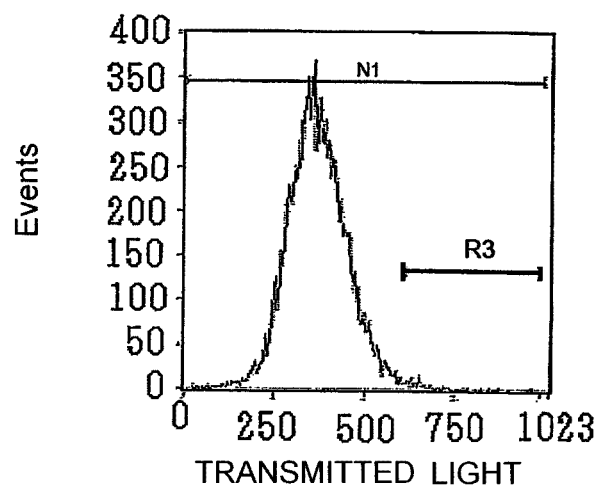
FIG. 14 is a histogram based on data of the region R1 of FIG. 12, where the abscissa axis indicates the peak of transmitted light in the transmitted light information.

Next, regarding the data within the R1 region, FIG. 14 illustrates a histogram where the abscissa axis indicates the peak of the transmitted light in the transmitted light information. A region of 1% from the largest value (right end of the figure) is called R3, and the number of data in the R3 region was 154 data. The mean value of the R3 region was 673.9 and the standard deviation ($\sigma$) was 69.9. The ratio (CV) of the standard deviation (o) to the mean value was 10.4%. On the other hand, the mean value of the entire region of FIG. 14 was 371.5, and the mean value of the entire region is at a distance of 4$\sigma$ from the mean value of the region R3.

Figure 15:
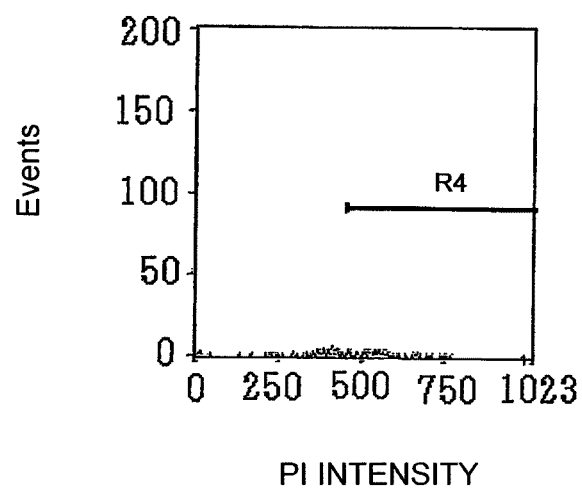
FIG. 15 is a histogram for a gated region of a region R3, where the abscissa axis indicates fluorescent intensity of a cell nucleus.

Next, regarding the gated region of the region R3, FIG. 15 illustrates a histogram where the abscissa axis indicates the fluorescent intensities of cell nuclei. The same region as the region R2 of FIG. 13 that is illustrated in FIG. 15 is called R4. The number of data of the region R4 was 74, and the gated data of the region R3 was 48.1%. As clearly understood from the above, it was possible to verify that the 1% or the half thereof from the region having a larger value in the transmitted light information (peak of the waveform of the transmitted light) was allopoid•pollyploid-nucleate cells. Accordingly, distinguishing and sorting of alloploid•polyploid-nucleate cells can be performed with high accuracy.

Figure 16:
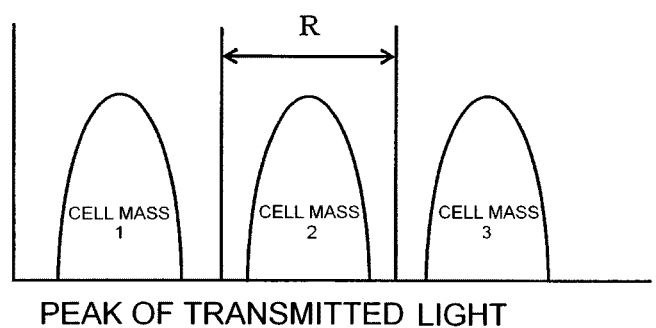
FIG. 16 is a histogram obtained by measuring a population in which plural kinds of cells are mixed, where the abscissa axis indicates transmitted light information.

The above description relates to an example in which a single species of cells is measured as a population, but a population in which plural species of cells is mixed may be considered. FIG. 16 illustrates a histogram obtained by measuring the populations in each of which plural species of cells are mixed. The abscissa axis indicates the peak in the transmitted light information and the vertical axis indicates the frequency. In the histogram of FIG. 16, if the populations of respective cells can be separated, an arbitrary region among the regions is determined, and the above-described analysis may be applied to the populations of cells within the region. That is, among the populations in each of which plural species of cells are mixed, an arbitrary region R is determined, the analysis of the present example may be applied to Cell Mass 2 within the region R.

In Examples 1 to 6, the peak of the transmitted light information and the peak of the scattering light information are used. However, the peak, the width, and the area of the transmitted light information, and the peak, the width, and the area of the scattering light information may be used.

As described above, according to the invention, regardless of an antibody•antigen reaction at the cell surface, expression of fluorescent protein in the cell, and the presence of fluorescent processing such as nuclear staining, a specific mass of living cells can be analyzed. In addition, as shown in Examples 1 to 6, regardless of the presence of the fluorescent processing, a specific cell mass or a part of living cells in the specific cells mass can be distinguished and sorted without performing a fluorescent labeling process such as nuclear staining.

As described above, in the method of distinguishing and sorting cells according to the invention, a beam mask or the like is used to block light before the light enters a detector, so that the laser beam that has passed through the flow cell without scattering and headed forward straight is used as transmitted light information, and living cells at a specific phase of a cell cycle of living cells and alloploid•polyploid-nucleate cells can be distinguished and sorted.

The invention claimed is:

1. A method of distinguishing and sorting cells, comprising:
    irradiating living cells with light;
    receiving transmitted light that is transmitted through the living cells;
    processing the transmitted light to obtain transmitted light information;
    receiving at least one of side-scattering light and fluorescent light from the living cells that are irradiated with light;
    processing the at least one of the side-scattering light and the fluorescent light to obtain one or both of side-scatter light information and fluorescent light information; and
    distinguishing and sorting a specific cell mass or a part of the living cells in the specific cell mass by using the transmitted light information and one or both of the side-scattering light information and the fluorescent light information, wherein one or both of the side-scattering light information and the fluorescent light information indicates the characteristics of the internal structures of the living cells, and the transmitted light information indicates at least one of: (a) morphological characteristics of the living cells, including at least one of size and shape of the living cells, and (b) characteristics of internal structures of the living cells,
    wherein the specific cell mass or the part of the living cells in the specific cell mass is distinguished and sorted, regardless of a presence of fluorescent processing that includes an antibody-antigen reaction at a cell surface and a presence of an expression of fluorescent protein in a cell being performed on the part of the living cells in the specific cell mass,
    the part of the living cells in the specific mass includes stem cells and cells at an S phase of the cycle are distinguished using the transmitted light information, and
    the stem cells that are bigger than a biggest cell at the S phase are sorted by using a histogram of cells where an abscissa axis indicates the transmitted light information, or by using an analytical dispersion diagram of cells where an abscissa axis indicates the transmitted light information and a vertical axis indicates the side-scattering light information, the transmitted light information, or the fluorescent light information.

2. The method of distinguishing and sorting cells according to claim 1, further comprising:
    sorting one cell from the part of the living cells in the specific cell mass in one well.

3. The method of distinguishing and sorting cells according to claim 1, wherein the part of the living cells in the specific cell mass is a part of the living cells at a G1 phase of a cell cycle.

4. A method of distinguishing and sorting cells, comprising:
    irradiating living cells with light;
    receiving transmitted light that is transmitted through the living cells;
    processing the transmitted light to obtain transmitted light information; and
    distinguishing and sorting a specific cell mass or a part of the living cells in the specific cell mass by using the transmitted light information, the transmitted light information indicating at least one of: (a) morphological characteristics of the living cells, including at least one of size and shape of the living cells, and (b) characteristics of internal structures of the living cells, wherein the specific cell mass or the part of the living cells in the specific cell mass is distinguished and sorted, regardless of a presence of fluorescent processing that includes an antibody•antigen reaction at a cell surface and a presence of an expression of fluorescent protein in a cell being performed on the part of the living cells in the specific cell mass, the part of the living cells in the specific mass includes stem cells and cells at an S phase of the cycle are distinguished using the transmitted light information, and the stem cells that are bigger than a biggest cell at the S phase are sorted by using a histogram of cells where an abscissa axis indicates the transmitted light information.

5. The method of distinguishing and sorting cells according to claim 4, further comprising:

sorting one cell from the part of the living cells in the specific cell mass in one well.

\* \* \* \* \*